United States Patent [19]
Ichijo et al.

[11] Patent Number: 5,731,200
[45] Date of Patent: Mar. 24, 1998

[54] ISOLATED NUCLEIC ACID ENCODING RECEPTOR-LIKE TGF-β1 BINDING PROTEIN

[75] Inventors: Hidenori Ichijo; Kohei Miyazono; Lars Ronnstrand; Ulf Hellman; Christer Wernstedt; Carl-Henrik Heldin, all of Uppsala, Sweden

[73] Assignee: Ludwig Institute for Cancer Research, New York, N.Y.

[21] Appl. No.: 567,538

[22] Filed: Dec. 5, 1995

Related U.S. Application Data

[60] Division of Ser. No. 167,939, filed as PCT/US92/05199, Jun. 18, 1992, Pat. No. 5,578,703, which is a continuation-in-part of Ser. No. 717,316, Jun. 18, 1991, Pat. No. 5,229,495.

[51] Int. Cl.$^6$ .................. C07M 21/04; C07K 14/71; C07K 14/715; C12N 15/12
[52] U.S. Cl. .................. 435/365; 435/69.1; 435/325; 435/365; 536/23.5
[58] Field of Search .................. 530/350; 435/69.1, 435/240.2, 252.3, 254.11, 325, 365; 536/23.1; 514/8

[56] References Cited

U.S. PATENT DOCUMENTS 5,229,495 7/1993 Ichijo et al. .................. 530/350

FOREIGN PATENT DOCUMENTS 63-150300 6/1988 Japan.
9205199 12/1992 WIPO.

OTHER PUBLICATIONS

Cheifetz et al. 1992, J. Biol. Chem. 267, 19027.
Ichijo, H et al., 1993, J. Biol. Chem. 268, 14505.
Gougos et al. 1990, J. Biol. Chem. 265,8361.
Horikawa et al. 1983 Nature 306,611.
Ishii et al. 1985 Proc. Natl. Acad. Sci. USA 82,4920.
Baker et al. 1988 Proc. Natl. Acad. Sci. USA 85,3294.
Lin, et al., "Receptors for the TGF–β superfamily: multiple polypeptides and serine/threonine kinases," *Reviews, Cell Biol.* 3: 14–19 1992).
Lin, et al., "Expression Cloning of TGF–β Receptors," *Mol. Reprod. & Cell Develop.* 32: 105–110 (1992).
Kanzaki, et al., "TGF–β Binding Protein: A Component of the Large Latent Complex of TGF–β with Multiple Repeat Sequences," *Cell* 61: 1051–1061 (*Jun. 16, 1990*).
Miyazono, et al., "Role for carbohydrate structures in TGF–β1 latency," *Nature* 338: 158–160 (*Mar. 9, 1989*).
Wakefield, et al., "Latent Transforming Growth Factor–β from Human Platelets," *J. Biol. Chem.* 263: 7646–7654 (1988).
Miyazono, et al., "Latent High Molecular Weight Complex of Transforming Growth Factor β1," *J. Biol. Chem.* 263: 6407–6415 (1988).
Cheifetz, et al., "The Transforming Growth Factor–β System, a Complex Pattern of Cross–Reactive Ligands and Receptors," *Cell* 48: 409–415 (1987).
Cheifetz, et al., "Cellular Distribution of Type I and Type II Receptors for Transforming Receptors for Transforming Growth Factor–β," *J. Biol. Chem.* 261: 9972–9978 (1986).
Massaqué, et al., "Cellular Receptors for Type β Transforming Growth Factor," *J. Biol. Chem.* 260: 2636–2645 (1985).

*Primary Examiner*—David L. Fitzgerald
*Assistant Examiner*—Mukul Ranjan
*Attorney, Agent, or Firm*—Felfe & Lynch

[57] ABSTRACT

The invention relates to a family of substantially pure, receptor like TGF-β1 binding glycoproteins. These molecules are characterized by molecular masses of 160 kd, 70–80 kd, and 30–40 kd as determined by SDS-PAGE, and the ability to bind the TGF-β1 molecule. This family of molecules is useful in identifying and/or quantifying TGF-β1 in a sample, as well as inhibiting its effect on cells. Also described are nucleic acid sequences which code for the protein monomer making up the molecules.

8 Claims, 12 Drawing Sheets kDa

```
GCGATGGACACACGCGGAGTGGCCGCGGCCATGAGGCCCCTGGTCCTGCTCGTTGCCTTC    60
    M  D  T  R  G  V  A  A  A  M  R  P  L  V  L  L  V  A  F
CTGTGCACCGCAGCCCCAGCCCTCGACACCTGTCCAGAGGTCAAGGTGGTGGGTCTGGAG   120
 L  C  T  A  A  P  A  L  D  T  C  P  E  V  K  V  V  G  L  E
GGCTCGGACAAGCTCTCCATCCTCCGAGGCTGCCCGGGGCTGCCTGGAGCCGCAGGGCCC   180
 G  S  D  K  L  S  I  L  R  G  C  P  G  L  P  G  A  A  G  P
AAGGGAGAGGCGGGCGCCAGTGGACCGAAGGGAGGACAAGGCCCTCCCGGAGCCCCTGGG   240
 K  G  E  A  G  A  S  G  P  K  G  G  Q  G  P  P  G  A  P  G
GAGCCAGGACCCCCGGGCCCAAAGGAGACCGAGGGGAGAAGGGCGAGCCTGGACCAAAA    300
 E  P  G  P  P  G  P  K  G  D  R  G  E  K  G  E  P  G  P  K
GGAGAGTCTTGGGAAACCGAGCAGTGTCTCACAGGACCTCGGACCTGCAAGGAGCTGCTG   360
 G  E  S  W  E  T  E  Q  C  L  T  G  P  R  T  C  K  E  L  L
ACCAGGGGGCACATTCTGAGCGGCTGGCACACCATCTACCTGCCAGACTGCCAGCCCCTG   420
 T  R  G  H  I  L  S  G  W  H  T  I  Y  L  P  D  C  Q  P  L
ACGGTGCTGTGTGACATGGACACGGATGGCGGGGGGTGGACCGTTTTCCAGCGCAGGAGC   480
 T  V  L  C  D  M  D  T  D  G  G  W  T  V  F  Q  R  R  S
GACGGGTCGGTGGACTTCTACCGGGACTGGGCCGCGTACAAGCGGGGCTTCGGCAGTCAG   540
 D  G  S  V  D  F  Y  R  D  W  A  A  Y  K  R  G  F  G  S  Q
CTGGGAGAGTTCTGGCTGGGGAACGACCACATCCACGCCCTGACGGCCCAGGGAACCAAT   600
 L  G  E  F  W  L  G  N  D  H  I  H  A  L  T  A  Q  G  T  N
GAGCTCCGGGTGGACCTCGTGGACTTCGAGGGCAACCACCAGTTTGCCAAGTACAGGTCC   660
 E  L  R  V  D  L  V  D  F  E  G  N  H  Q  F  A  K  Y  R  S
TTCCAGGTGGCAGACGAGGCAGAGAAGTACATGCTGGTCCTGGGAGCCTTTGTAGAGGGC   720
 F  Q  V  A  D  E  A  E  K  Y  M  L  V  L  G  A  F  V  E  G
AATGCAGGTGATTCCCTGACGTCCCACAACAACAGCCTGTTCACCACCAAAGACCAGGAC   780
 N  A  G  D  S  L  T  S  H  N  N  S  L  F  T  T  K  D  Q  D
AACGACCAGTACGCCTCAAATTGTGCAGTGCTGTACCAGGGAGCCTGGTGGTACAACAGC   840
 N  D  Q  Y  A  S  N  C  A  V  L  Y  Q  G  A  W  W  Y  N  S
TGTCACGTGTCCAACCTGAACGGCCGCTACCTCGGGGGCTCGCACGGGAGCTTTGCAAAC   900
 C  H  V  S  N  L  N  G  R  Y  L  G  G  S  H  G  S  F  A  N
GGCGTCAACTGGAGTTCGGGGAAAGGGTACAACTACAGCTACAAGGTGTCGGAGATGAAG   960
 G  V  N  W  S  S  G  K  G  Y  N  Y  S  Y  K  V  S  E  M  K
TTTCGGGCCACCTAGGGCGGGACAGTGCTTCCAGAACCCTCCCTGGGGAGGGGCCACGGG  1020
 F  R  A  T
GCTCCCGCTCACTATCCGCCCGGGTGTGAAGGGCCACATCCCAACCCTGGGGGGCGGCCA  1080

TGCCCTCTGCACCTCCACCAGCTTCCAATCTTCTGTCCCTCTCAGGAGGACAAGAGTGAC  1140

CGTTACTCCAGCAACATGTATTCTCAATAAAGACACTTGCTTACCCAAAAAAAAAA     1196
```

ISOLATED NUCLEIC ACID ENCODING RECEPTOR-LIKE TGF-β1 BINDING PROTEIN

This application is a divisional of U.S. patent application Ser. No. 08/167,939, filed as PCT/US92/05199 on Jun. 18, 1992, now U.S. Pat. No. 5,578,703, which is a continuation in part of application Ser. No. 07/717,316, filed Jun. 18, 1991, now U.S. Pat. No. 5,229,495.

FIELD OF THE INVENTION

This invention relates to protein biochemistry. More particularly, it relates to molecules which bind to the substance known as transforming growth factor-β1 ("TGF-β1" hereafter). The invention also relates to nucleic acid molecules coding for the protein, and uses thereof.

BACKGROUND AND PRIOR ART

A family of molecules is referred to as the "TGF-βs". These are 25 kd dimeric proteins which have multifunctional effects on growth and differentiation of cells, both in vitro and in vivo. See Roberts et al. in Peptide Growth Factors And Their Receptors I (Sporn et al., eds., pp 419–472; Springer-Verlag, Berlin, 1990); Moses et al., Cell 63: 245–247 (1990); Massagué, Ann. Rev. Cell. Biol. 6: 597–641 (1990). The family contains at least three different, structurally related members, identified as "β1, β2 and β3". Many other proteins are more distantly related, including bone morphogenic proteins, Müllerian inhibitory substance, activins, inhibins, and so forth.

Originally the TGF-β family of proteins was identified as being involved in increasing anchorage independent growth of normal rat kidney cells; however, the proteins are also recognized as a potent growth inhibitors for diverse cell types, including hematopoietic cells, lymphocytes, epithelial and endothelial cells (Ohta et al., Nature 329: 539–541 (1987); Kehri et al., J. Immunol 137: 3855–3860 (1986); Moses et al., in Cancer Cells 3 (Feramisco et al., ed; Cold Spring Harbor, N.Y., 1985); pg. 65–71; Baird et al. Biochem. Biophys. Res. Commun 138: 476–482 (1986); Frater-Schröder et al., Biochem. Biophys. Res. Commun. 137: 295–302 (1986); Heimark et al., Science 233: 1078–1080 (1986)). The molecules have a dramatic effect on accumulation of extracellular matrix proteins (Massagué, supra), and have been implicated in pathogenic glomerulonephritis (Border et al., Nature 346: 371–374 (1990)); liver cirrhosis (Castilla et al., N. Eng. J. Med. 324: 933–940 (1990)); and pulmonary fibrosis (Khalil et al., in Clinical Application of TGF-β1 (Bock et al., ed. Ciba Foundation Symposium 157, John Wiley & Sons, 1991, pg. 194–211).

The TGF-β family interacts with other proteins on several levels. One of these is mediation of binding via cell surface receptors. The art recognizes three distinct high affinity receptors for TGF-βs, referred to as types I, II and III. The first two of these have molecular masses of 53 and 70–85 kd, respectively, while the third is denoted "betaglycan" because of its proteoglycan like structure, and is further characterized by a molecular mass of 200–400 kd. Massagué et al., in Transforming Growth Factor-βs: Chemistry, Biology and Therapeutics (Piez et al., eds., Ann. N.Y. Acad. Sci. 593, 1990), pg. 59–72; Segarini et al., in Clinical Applications of TGF-β (Bock et al., eds. Ciba Foundation Symposium 157, John Wiley & Sons, 1991, pg 29–50). The betaglycan molecule is a membrane proteoglycan, having a 100–140 kd core protein with unknown functional importance, while type I and II receptors appear to be involved in transduction of TGF-β cellular effect. Segarini et al., J. Biol. Chem. 263: 8366–8370 (1988); Cheifetz et al., J. Biol. Chem. 263: 16884–16991 (1988); Massagué et al., supra. Some cell lines express only type I receptors and are inhibited by TGF-β1. These include hematopoietic progenitor cell lines (Ohta et al., supra) and squamous cancer cell lines (Ichiyo et al., Exp. Cell Res. 187: 263–269 (1990)). Mutant cell lines of mink epithelial cells have been shown to have lost or to have anomalous expression of type I and/or type II receptors (Boyd et al., J. Biol. Chem. 264: 2272–2278 (1989); Laiho et al., J. Biol. Chem. 265: 18518–18524 (1990)).

Additional binding molecules for TGF-β having molecular masses of 60 kd, 85–320 kd, and 400 kd have been reported in pituitary tumor cell lines, rat glomeruli, and bovine liver cells, respectively, as reported by Cheifetz et al., J. Biol. Chem. 263: 17225–17228 (1988); Mackay et al., J. Biol. Chem. 265: 9351–9356 (1990); O'Grady et al., J. Biol. Chem. 266: 8583–8589 (1991).

On another level, the precursors of TGF-β, especially TGF-β1, interact with protein molecules known as the latent TGF-binding protein or "LTBP". The interaction yields a high molecular weight, inactive complex which is secreted from the cell. This is sometimes referred to as the latent TGF-β1 complex. See Miyazono et al., J. Biol. Chem. 263: 6407–6415 (1988); Pircher et al., Biochem. Biophys. Res. Commun. 136: 30–37 (1984); Wakefield et al., J. Cell Biol. 105: 965–975 (1987). The inactive or latent complexes contain a non-covalent association of TGF-β1, a disulphide bonded complex of a dimer of N-terminal peptide of TGF-β1 precursor and as third component, the LTBP. This third component occurs as a molecule with a molecular mass which may range from 125–190 kds. Experiments have shown that the binding proteins do not inactivate TGF-β1.

The molecules discussed supra are sometimes referred to as "binding proteins", because they do, in fact bind to the TGF-β1 precursor. A fundamental difference between these molecules and the molecules of the invention is that while the prior art molecules may be referred to as "synthesis" binders, it is more appropriate to describe the invention as involving "effector" binders. The synthesis binders are involved in the "packaging" of TGF-β1 in the cell, such that it is released for subsequent activities. When bound to the prior art molecules, TGFs are essentially inert. In contrast, the protein containing molecules of the invention may be seen as "effectors" in that TGF-β1 binds directly to these, so as to effect a response thereby. This distinction should be kept in mind in connection with this application.

It is an object of the invention to describe these substantially pure, receptor like TGF-β1 binding protein containing molecules, which are characterized by molecular masses of 160 kd, 70–80 kd, and 35–40 kd as determined by SDS-PAGE, as well as their uses in various processes. The ranges are due to the behavior of the species under reducing and non-reducing conditions, as will be seen infra. It is also due to the nature of the molecule's structure, which is as a monomer, dimer or trimer based upon a single peptide. The implication of this structure are discussed infra.

The objects of the invention discussed supra as well as others will be seen from the disclosure which follows.

DETAILED DESCRIPTION OF PREFERRED EMBODIMENTS

Example 1

Figure 1:
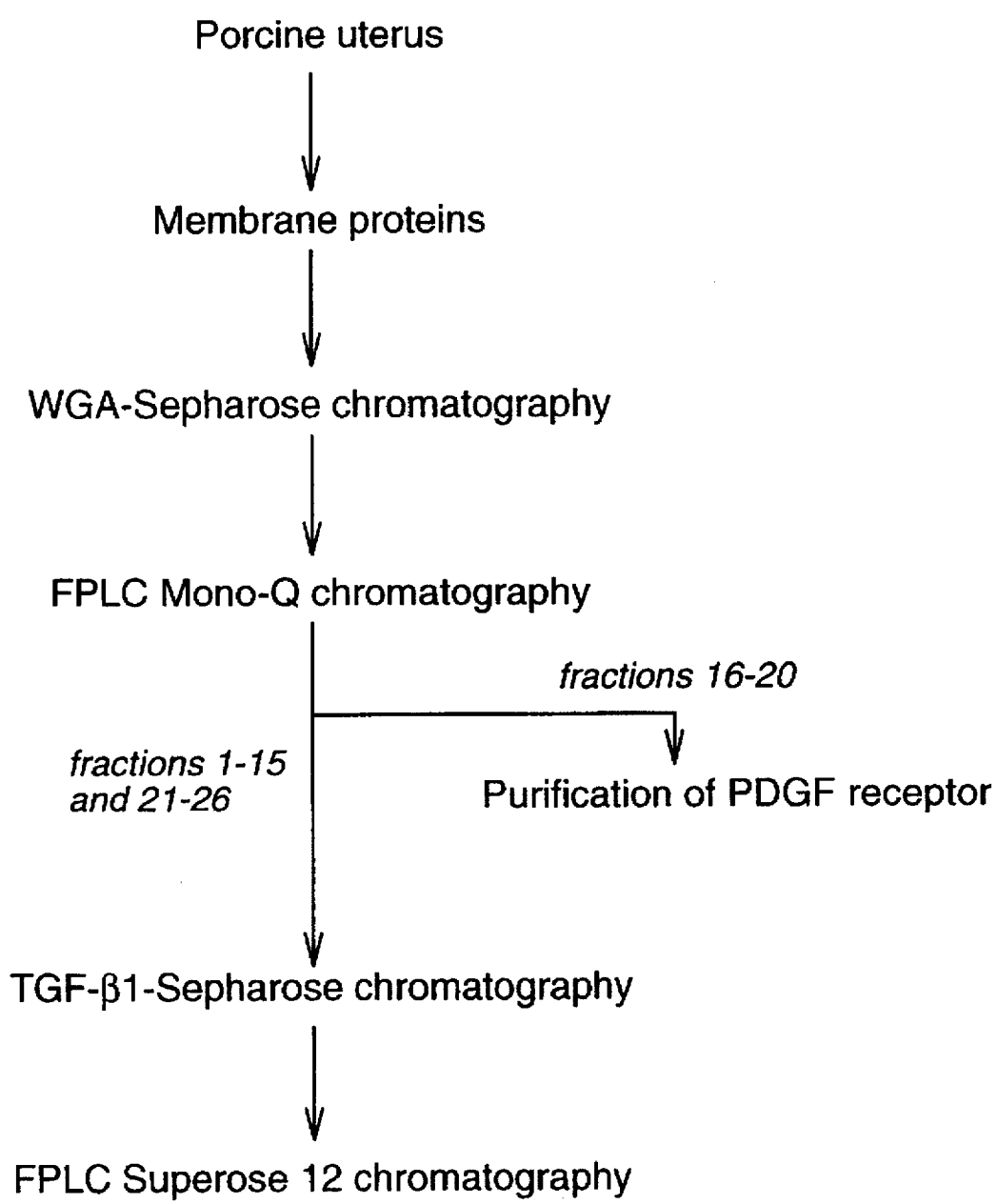
FIG. 1 provides a schematic outline of the purification protocol used to isolate the substantially pure receptor like transforming growth factor β1 binding proteins of the invention.
Figure 2:
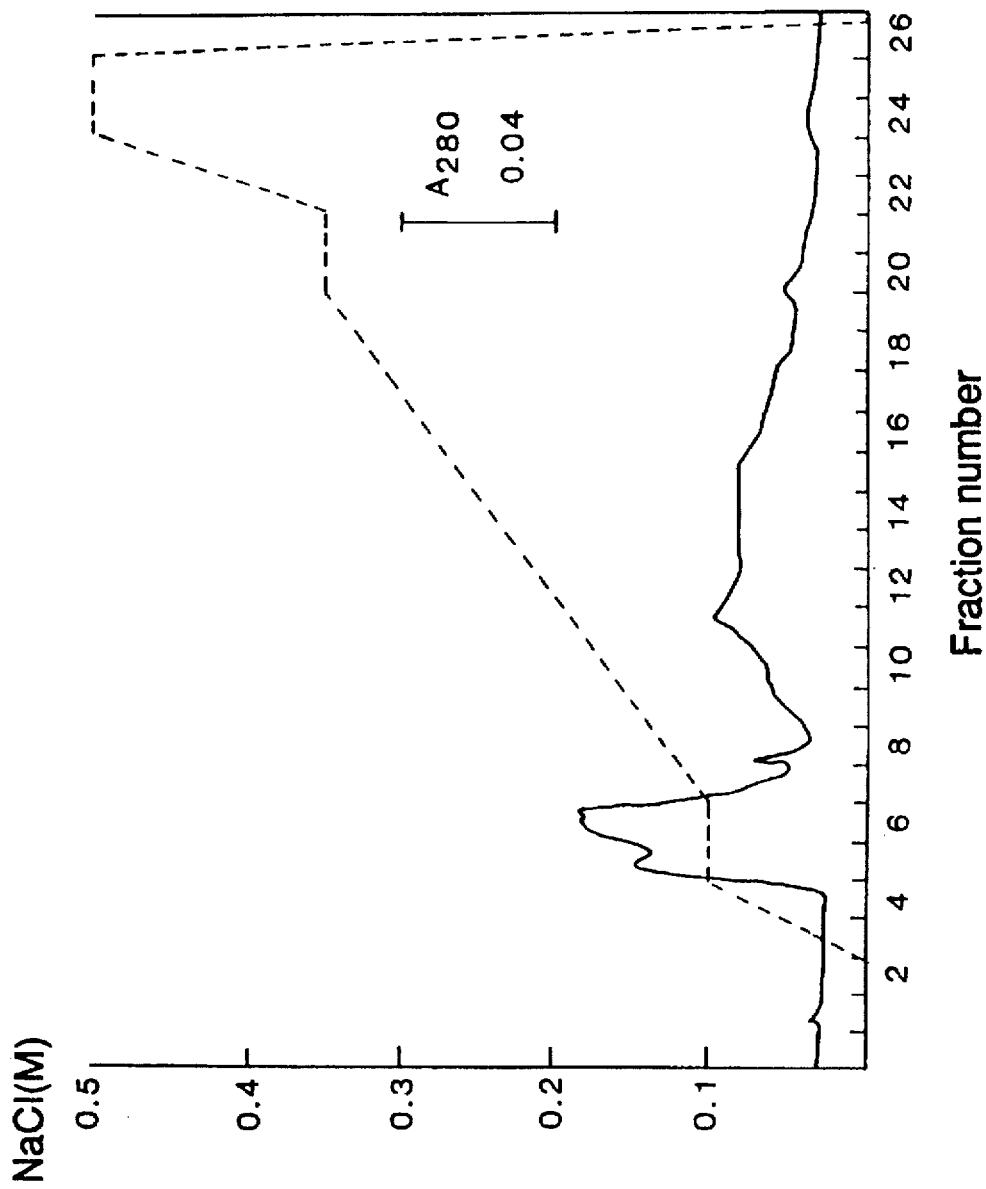
FIG. 2 shows a protein profile of a representative FPLC run for the binding proteins of the invention.

A protocol originally described by Rönnstrand et al., J. Biol. Chem. 262: 2929–2932 (1987) for purifying PDGF receptor was followed. Briefly, porcine uterus tissue was used as starting material for preparation of membranes. Differential centrifugation following Rönnstrand, supra, was used to obtain the membranes. The membrane proteins were then solubilized in Triton X-100®, and subjected to chromatography on wheat germ agglutinin Sepharose and fast protein liquid chromatography Mono-Q columns. First, the proteins were purified on the wheat germ agglutinin column, and the purified material was then applied to an FPLC Mono Q column, using increasing concentrations of NaCl. Twenty-six fractions were taken from the column. Of these, fractions 16–20 were pooled and used to purify PDGF receptor; the other fractions were stored at −20° C. and used as starting material to purify the receptor like binding proteins of the invention. FIG. 2 shows the concentration of NaCl used for each fraction, via the dotted line. Fractions 16–20 were used for PDGF purification.

Example 2

To remove the receptor like binding proteins from the fractions obtained following Example 1, a TGF-β1 Sepharose column was prepared. This was accomplished using recombinant TGF-β1 purified from conditioned medium of CHO cells, transfected with human TGF-β1 cDNA. One mg of TGF-β1 was coupled to 0.5 g of cyanogen bromide activated Sepharose 4B, to yield about 0.67 mg of TGF-β1/ml of gel.

Following preparation of the column, fractions 1–15 and 21–26 from example 1 were thawed, pooled, and dialyzed against binding buffer (0.2% Triton X-100®, 125 mM NaCl, 5 mM KCl, 5 mM MgSO$_4$, 1.2 mM CaCl$_2$, 20 mM HEPES, pH 7.4). Twenty-five ml amounts of dialyzed sample were then mixed with 2.5 ml of the previously prepared Sepharose beads, and the resulting suspension was incubated overnight at 4° C., with gentle shaking. The beads were then collected in a column which was then washed with 25 ml of binding buffer, and then 25 ml of binding buffer with 500 mM NaCl. Bound molecules were then eluted with 5 ml of a solution of 0.2% Triton X-100®, 500 mM NaCl, in 100 mM sodium acetate buffer, pH 5.5, followed by 5 ml of 0.2% Triton X-100®, 500mM NaCl, and 100 mM acetic acid at pH 3.5, to yield what will be referred to as the "pH 3.5 eluate" hereafter.

Example 3

The pH 3.5 eluate fractions from four to six chromatography runs, as discussed supra, were pooled and mixed with four volumes of acetone. The protein portion was precipitated at −20° C. for 60 minutes, followed by centrifugation at 17,000×g at 4° C. for 20 minutes. The resulting protein pellets were dried, resuspended in 500 ul of 70% formic acid, followed by application to an FPLC Superose 12 column which had been pre-equilibrated and eluted with 70% formic acid at a flow rate of 0.5 ml/min. Fractions (250 ul) were collected, and aliquots of individual fractions were lyophilized and subjected to further analysis.

Example 4

Fractions obtained following example 2 were examined for $^{125}$I-TGF-β1 binding, using affinity cross linking and "in gel" binding procedures.

To do this, 50 ul portions of the individual Mono-Q fractions were incubated for three hours at 4° C. in the presence of 1 nM of recombinant TGF-β1 labeled with $^{125}$I following Frolik et al., J. Biol. Chem. 259: 10995–11000 (1984), to yield a product with 5×10$^6$ cpm/ml. The incubation took place with fractions that either had been dialyzed against the binding buffer described supra, or dissolved in it.

Figure 3:
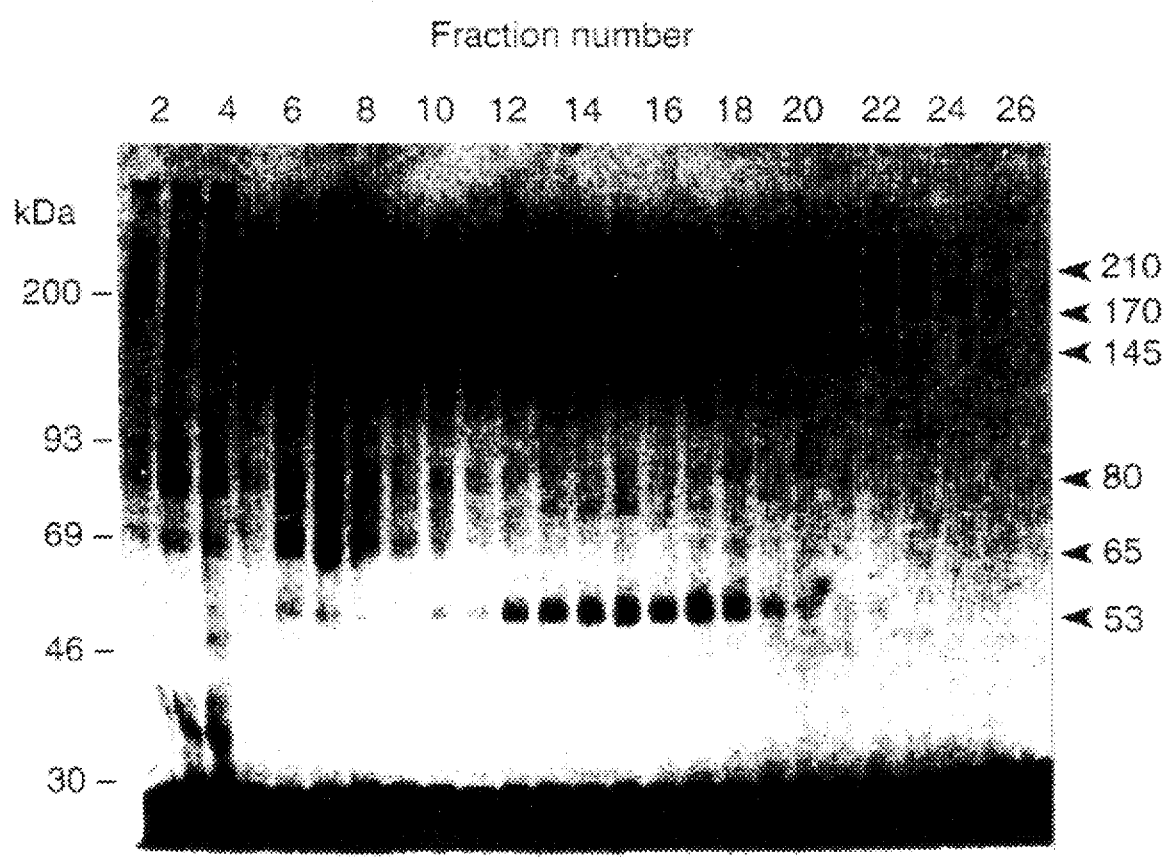
FIG. 3 shows SDS gel runs for various fractions prepared according to the invention, following affinity cross linking with $^{125}$I-TGF-β1.

The affinity labeled proteins were then cross-linked using 0.14 mM of disuccinimidyl suberate ("DSS") for 15 minutes at 4° C. The cross-linking reaction was quenched by adding SDS-electrophoresis sample buffer containing 80 mM Tris. In this and in following examples, the samples were then heated at 95° C. for three minutes in SDS-sample buffer which did or did not contain 10 mM dithiothreitol (DTT). The samples were then applied to 5–15% SDS-polyacrylamide gels following Blobel et al., J. Cell Biol. 67: 835–851 (1975) for electrophoresis, under either reducing or non-reducing conditions. Gels were then fixed in 25% methanol, 7.5% acetic acid, dried and subjected to 12-days of autoradiography using Fuji X-ray film. The results of the autoradiography are shown in FIG. 3.

Example 5

Experiments were also carried out to study "in gel" binding using radiolabeled TGF-β1. To do this, the method described by Murphy et al., Anal. Biochem. 187: 197–201 (1990) for $^{125}$I heparin, was used with some minor modifications. To summarize, 250 ul of individual fractions were lyophilized and subjected to non-reducing SDS gel electrophoresis. Following SDS-gel electrophoresis, gels were fixed for 30 minutes in 40% methanol, 7% acetic acid, and rinsed several times with distilled water. The gels were then incubated overnight with 10% ethanol, 10 mM Tris-HCl, pH. 7.5 at 4° C. with gentle shaking, followed by washing for one hour with the same buffer. The gels were then incubated for 30 minutes with binding buffer containing bovine serum albumin (BSA) at 2 mg/ml. Gels were then transferred to plastic bags with 10 ml binding buffer containing 1×10$^6$ cpm of $^{125}$I-TGF-β1 and 2 mg/ml of BSA. These bags were sealed and shaken overnight at 4° C.

Figure 4:
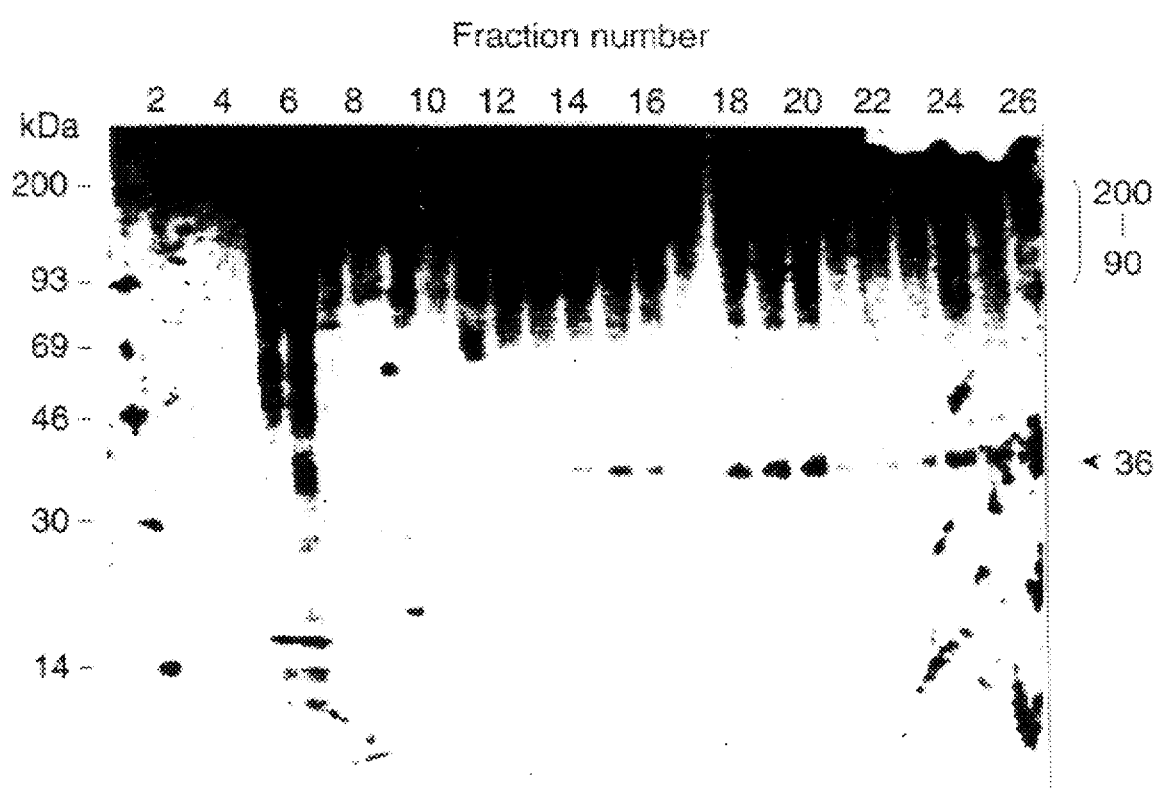
FIG. 4 depicts "in-gel" ligand binding of fractions following FPLC Mono-Q chromatography.

Excess $^{125}$I-TGF-β1 was removed, and the gels were then washed with 500 ml of binding buffer for 30 minutes, followed by two washes with 500 mM binding buffer containing 400 mM NaCl. Each wash was for 30 minutes. Following this, gels were dried and subjected to autoradiography as per example 4, but for three days. FIG. 4 shows these results.

In both of examples 4 and 5, $^{14}$C labeled molecular weight markers were used as follows: myosin (200 kd), phosphorylase B (92.5 kd) bovine serum albumin (69 kd), ovalbumin (46 kd), carbonic anhydrase (30 kd), lysozyme (14.3 kd).

The results from example 4 showed complexes of apparent molecular masses of 210,000; 170,000; and 145,000 kd from most of the fractions, as well as complexes with molecular masses of 80,000 and 65,000 in fractions 2–10, plus one of 53,000 in fractions 10–20. The results, presented in FIG. 4, showed several binding components in the 90–200 kd range in fractions 5–26, plus a prominent band of 36 kd in fractions 11–26.

Example 6

The results obtained in Example 4 gave a pattern which was similar to that observed by Seganini et al., J. Biol. Chem. 263: 8366–8370 (1988), and Cheifetz et al., J. Biol. Chem. 263: 16884–16991 (1988), for betaglycan affinity labeled with $^{125}$I-TGF-β1. To determine whether either of the 210 kd or 170 kd components represented betaglycan, samples were again cross linked with $^{125}$I-TGF-β1, and digested with heparinase and chondroitinase. The references cited to supra had shown that the proteoglycan betaglycan shifts to 100–140 kd following such treatments. The 210 and 170 kd complexes tested herein showed no such movement, strongly suggesting that they did not represent betaglycan.

Example 7

Once it had been shown that there was binding activity for the proteins of examples 1–6, further purification steps were carried out.

Again referring to the fractions obtained with the Mono-Q column, all but fractions 16–20 were combined and dialyzed against dialysis buffer as described supra. Again, following the protocols described supra the dialyzed material was subjected to affinity chromatography using immobilized TGF-β1. Following this, the column was washed with binding buffer, described supra, then with binding buffer at higher ionic strength, i.e., 0.5M NaCl. Following this, two elutions were carried out, first with an elution buffer at pH 5.5, and than at pH 3.5 Each fraction was analyzed on SDS-PAGE, using silver staining in the absence and presence of reducing agent.

Figure 5:
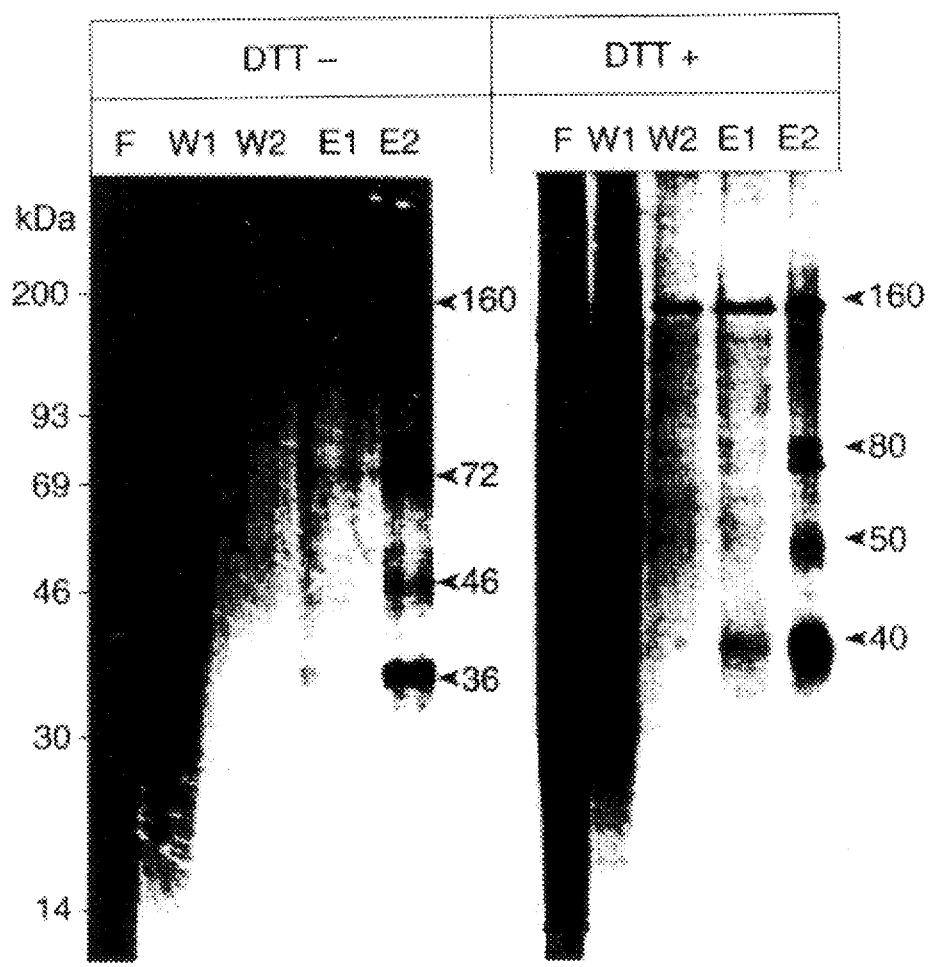
FIG. 5 shows SDS-gel electrophoretic analysis of fractions obtained following sepharose chromatography using TGF-β1.

The results from these different fractionations are shown in FIG. 5, where "FT" refers to the flow through material, "W1" to the low ionic strength wash, "W2" to the high ionic strength wash, "E1" to the eluate at pH 5.5, and E2 to the eluate at pH 3.5. Very little protein eluted at pH 5.5, while at pH 3.5 and under non reducing conditions, materials eluted which showed apparent molecular masses of 160, 72, 46 and 36 kilodaltons. When this fraction was tested under reducing conditions, species of apparent molecular masses of 160, 80, 50 and 40 kilodaltons were observed. This suggests that four separate species were present, having molecular weights of 160 kd, and ranging from 70–80 kd, 45–50 kd, and 35–40 kd.

Example 8

Figure 6:
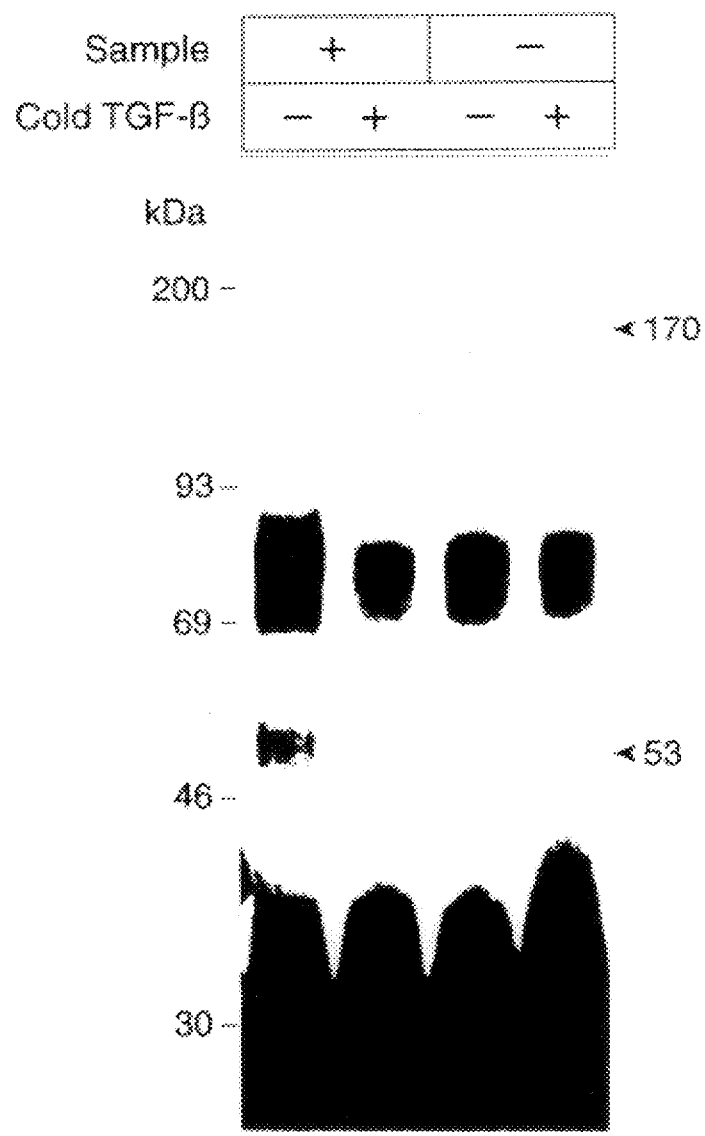
FIG. 6 presents analysis of the pH 3.5 elution fraction of TGF-β1 Sepharose chromatography, following affinity labelling using $^{125}$I-TGF-β1.

The pH 3.5 eluate clearly contained the material of interest, and was subjected to further analysis. An aliquot of the fraction was lyophilized, redissolved in binding buffer, and incubated with 1 nM $^{125}$I-TGF-β1, prepared as described supra, either without or with an excess amount of unlabeled TGF-β1 (400 nM). Again, following the protocols set forth supra, these materials were cross linked with DSS and analyzed via SDS gel electrophoresis under reducing conditions. Radiographic data from these experiments are presented in FIG. 6, and show complexes with apparent molecular weights of 170 and 53 kd. These complexes were associated with $^{125}$I-TGF-β1. This radiolabelled molecule has a molecular weight of 12.5 kd under reduced conditions, so it would appear that the binding materials are the 160 and 40 kd species of Example 7. Components of molecular mass 70–90 kd and 25 kd were also found, but there was no observed displacement even when 400 fold cold molar excesses of unlabeled TGF-β1 were used. Also, these bands were found in control lanes where samples were not present, suggesting free $^{125}$I-TGF-β1 and the labeled molecule non-specifically cross linked to BSA.

Example 9

Figure 7:
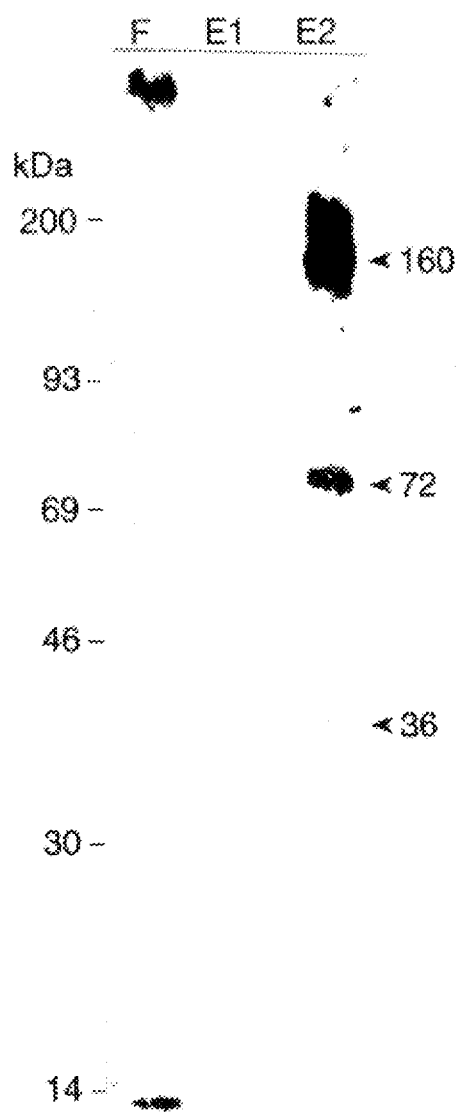
FIG. 7 presents an analysis of different TGF-β1 Sepharose chromatography fractions using "in-gel" ligand binding.

The pH 3.5 fraction was then used for "in gel" ligand binding, as were some of the other fractions. Specifically, 70 ul of FT, E1 and E2 fractions were subjected to the same protocol for in gel ligand binding as described previously. FIG. 7 shows these results. Two of the three components recognized were identical to components found using the affinity labeling experiment of Example 8. A third, an 80 kd band, may have been hidden in the diffuse 70–90 kd band shown in FIG. 6 and discussed in Example 8. A fourth component, a 50 kd band, was the material present in lowest quantity in the pH 3.5 fraction.

Example 10

The foregoing examples showed that there were several receptor like binding proteins present. In order to separate these, a size separation method was used. Specifically, pH 3.5 eluates from four to six TGF-β1 Sepharose chromatographies were pooled and subjected to acetone precipitation, as per Example 2, supra. Precipitates were dried, redissolved in 70% formic acid, and applied to an FPLC Superose 12 column eluted in 70% formic acid.

Figure 8:
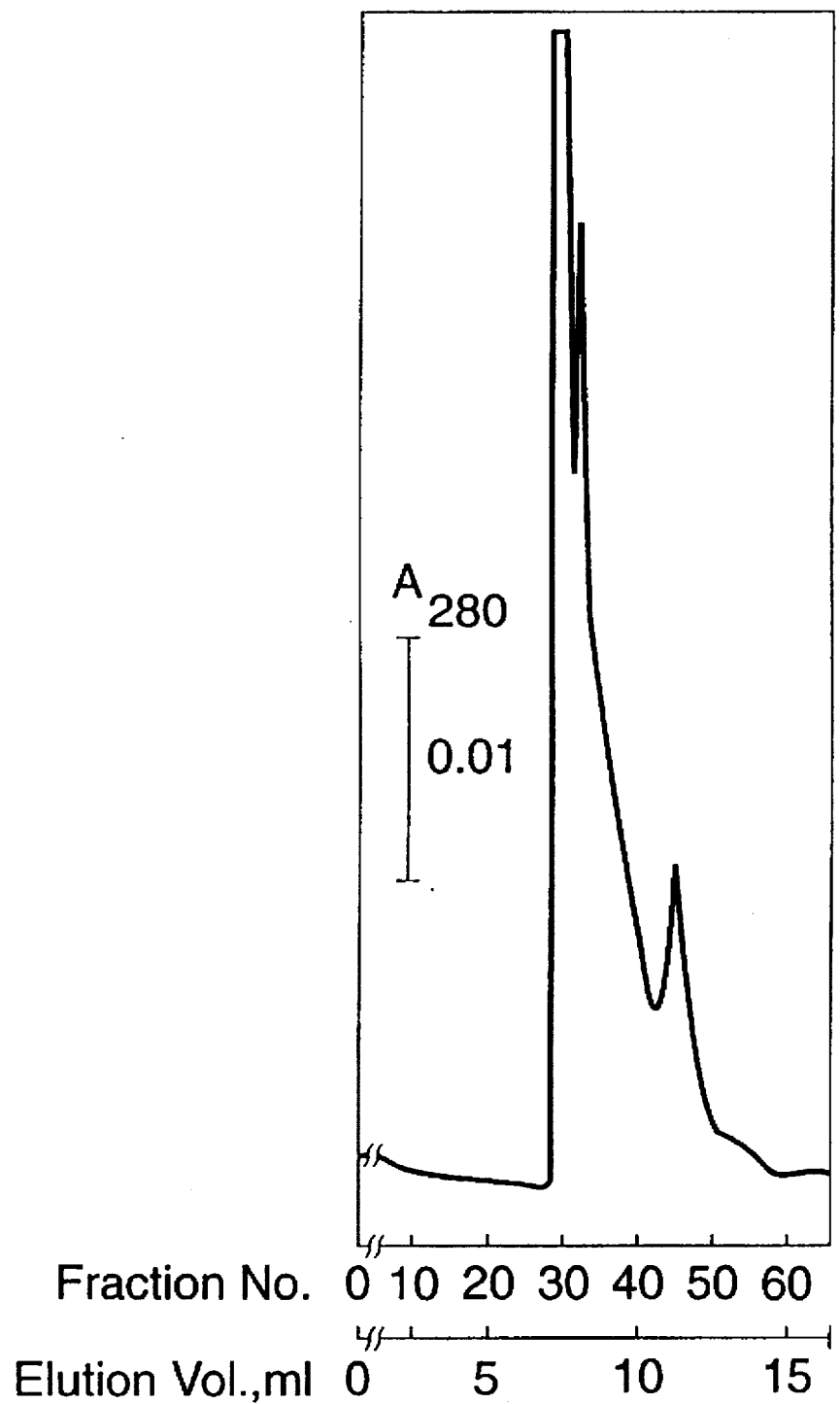
FIG. 8 is a protein profile of a chromatogram of the pH 3.5 elution fraction, following acetone precipitation concentration.

The protein profile of this chromatography is shown in FIG. 8, where three major protein peaks were found at fractions 28–31, 32–34, and 44–48. A shoulder was found at fractions 36–40.

Figure 9:
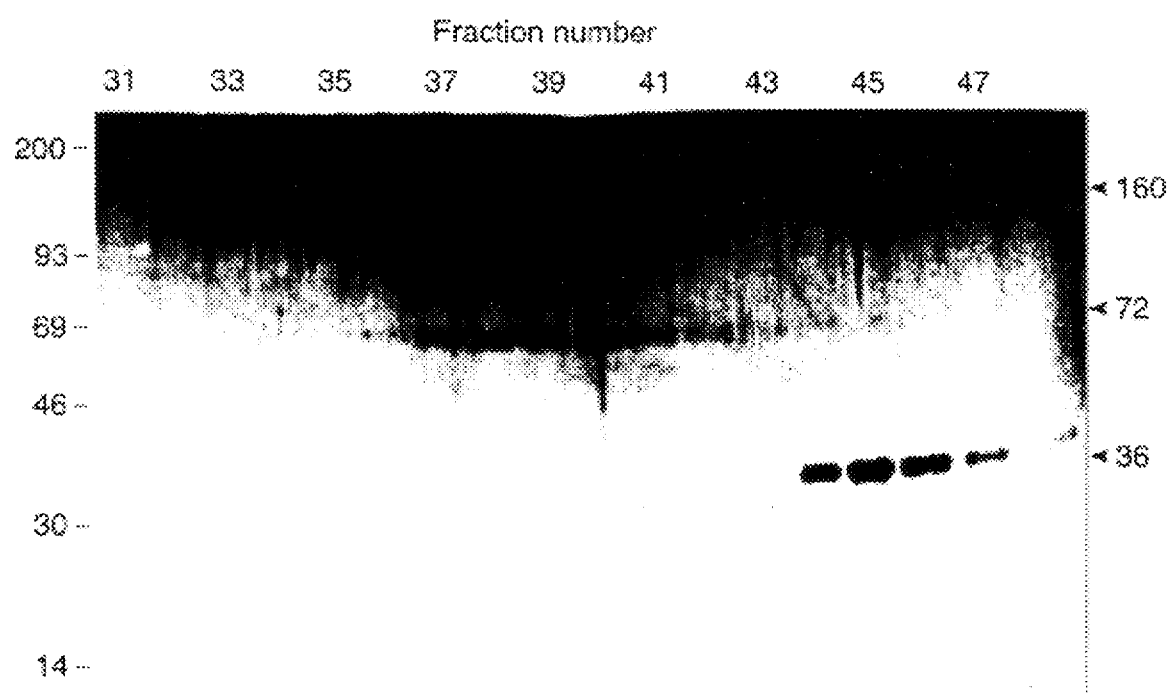
FIG. 9 is an SDS-gel analysis of various fractions obtained from Superose 12 chromatography.

Individual fractions 31–48 were then lyophilized and analyzed in 10 ul aliquots, using SDS-PAGE under non reducing conditions followed by silver staining. These results are shown in FIG. 9. They show that the 160 kd component eluted in a broad peak through fractions 32–42, while a 72 kd component eluted in fractions 37–40, and the 36 kd component in fractions 44–47. This last material was apparently homogeneous, and further analysis under reducing conditions showed a 40 kd fraction. These results indicate that this material is a single chain polypeptide, probably containing intra-chain disulphide bonds. The absorbance values at 280 nm in FIG. 8 suggest that about 12 ug of this 40 kd molecule can be purified from 10 kg of tissue.

Example 11

Figure 10:
FIG. 10 shows analysis of the pure 40 kd component of the analysis, using $^{125}$I-TGF-β1 affinity cross linking experiments.

The 40 kd molecule was analyzed to test its binding to TGF-β1, using the affinity cross-linking protocols set forth supra. FIG. 10 shows that this experiment yielded a 62 kd complex under non-reducing conditions, and a 53 kd complex when 10 mM of DTT are present. If the molecular mass of TGF-β1 under non-reducing and reducing conditions are subtracted (25 kd, 12.5 kd), the resulting figure is 40 kd.

Figure 11:
FIG. 11 shows in gel binding of the 40 kd receptor like binding protein.

Similarly, when "in-gel" binding under non-reducing conditions was carried out, a labeled band is found at 36 kd, as shown in FIG. 11. This is the expected value, and the results prove that the substantially pure receptor like binding protein for TGF-β1 having a molecular mass of 36–40 kd does bind the molecule when in homogeneous form.

Example 12

The initial purification work, as per Example 1, used a wheat germ agglutinin column, so it cannot be ruled out that the materials of interest are glycoproteins. To that end, the molecules of the invention are described as "protein containing" because they definitely contain a protein component, and may be glycoproteins. Analysis of the homogeneous 40 kd component using endoglycosidase F, using SDS PAGE, silver staining and reducing conditions yielded a 35 kd product, so the molecules may be glycoproteins.

Example 13

Tryptic digestion of the 40 kd material has revealed some amino acid data. The following sequences have been identified:

(I) V(D)LV(D)FEGNHQFA (SEQ ID NO: 2)

(II) VVGLEGSDKLSILR (SEQ ID NO: 3)

(III) VFGSQLGE (SEQ ID NO: 4)

where P* is hydroxyproline, and a bracketed amino acid means the determination is tentative. Sequence III has been used to prepare antiserum which specifically binds to all three glycoproteins.

Example 14

Additional experiments with the proteins described supra resulted in the generation of additional tryptic fragments. These included the following:

(1) YLGGSHGSFA (SEQ ID NO: 1)

(2) VVGLEGSDKLSILR (SEQ ID NO: 3)

(3) CP*GLP*GAAGP (SEQ ID NO: 6)

(4) DWAAY (SEQ ID NO: 7)

In SEQ ID NO: 6, P is hydroxy prolene an additional peptide was derived from lysine peptidase fragment digestion of a mixture of the 3 glycoproteins discussed supra.

R G F G S Q L G E F W L G N D H I H A L T A Q G T-NELXVDLVFEGNHQFA (SEQ ID NO: 8).

Example 15

Experiments were carried out to isolate a cDNA sequence coding for the protein of interest. In order to prepare a specific probe, degenerate oligomers were used based upon the peptide sequences presented in Example 13 and 14, in a polymerase chain reaction ("PCR") using mRNA derived from porcine uterus. Specifically the sequences

QLGEFW (SEQ ID NO: 9)

and

FEGNHQF (SEQ ID NO: 10)

were used to prepare sense and antisense degenerate oligomers:

```
5' CAA CTN GGN GAA TTT TGG-3'  (SEQ ID NO: 11)
       G T      G     C
                              (sense)

5' AAA TTG ATG ATT NCC TTC AAA-3'  (SEQ ID NO: 12)
   G C   G   G       C G
                              (antisense)
```

These degenerate oligomers were used in the polymerase chain reaction on the mRNA, and this led to the amplification of an approximately 100 base pair fragment. The 100 base pair fragment was subcloned into bluescript, and was then sequenced.

Example 16

Synthetic oligonucleotide probes were synthesized based on the 100 base pair sequence discussed supra:

5'-TTC TGG CTG GGG AAC GAC CAC ATC CAC GCC CTG ACG GCC CAG GGA-3' (SEQ ID NO: 13) (sense)

5' GAA GTC CAC GAG GTC CAC CCG GAG CTC ATT GGT TCC CTG GGC CGT-3' (SEQ ID NO: 14) (antisense).

These probes were labelled with [$^{32}\gamma$]P and were used to screen a cDNA library prepared from mRNA isolated from porcine uterus. The cDNA was inserted into λgt10 to form the library. The library was transferred onto nitrocellulose filters which were hybridized to the probes. The filters were washed with 2×SSC, 0.1% SDS at room temperature for 15 minutes, followed by 0.5×SSC, 0.1% SDS, 50° C. for 20 minutes, and a cDNA clone was isolated. The insert was short, so this clone was used to rescreen the library, using slightly higher stringency washes from the first set of conditions (2×SSC, 0.1% SDS, room temperature 15 minutes, followed by 0.2×SSC, 0.1% SDS, 60° C., twenty minutes).

The isolated cDNA clone was sequenced, and thus is presented in (SEQ ID NO: 5), attached hereto.

The foregoing experiments demonstrate the existence of several receptor like binding proteins for TGF-β1. The term "receptor like" is used to distinguish these molecules generically from other molecules which have been referred to as "TGF-β1 binding proteins". The previously described molecules are substances which are complexed to the TGF-β1 molecule intracellularly and appear to be necessary to permit extracellular passage of the TGF-β1. In contrast, there was no evidence of the molecules of this invention being complexed to TGF-β1 when isolated. As such, they show "receptor like" properties in that they bind to and remove TGF-β1 from solution, but "receptor" is generally used to refer to a membrane bound material which is involved in reception of the target molecule. There is no evidence to link the described and claimed molecules of the invention to such a role, thus they are referred to as "receptor-like" rather than receptors.

The data derived from the experiments reported herein supported the hypothesis that the TGF-β1 binding proteins described herein are related as monomer, dimer and timer of the amino acid molecule described in e.g., (SEQ ID NO: 5).

The molecules appear to be glycoproteins based upon their ability to bind to wheat germ agglutinin columns, and the size reduction of the 40 kd molecule following endoglycosidase treatment.

The three molecules do not appear to have proteoglycan structures and are, therefore, clearly distinct from type III TGF-β receptor, which is a proteoglycan and is referred to as "betaglycan". Additional comparison to, e.g., decorin (Yamaguchi et al., Nature 346: 281–284 (1990)); α2 macroglobulin (O'Connor-McCourt, et al., J. Biol. Chem. 262: 14090–14099 (1987)); and type IV collagen (Paralker et al., Dev. Biol. 143: 303–308 (1991)), are not warranted because all of these molecules have size and subunit compositions different from the molecules described herein, and are secreted molecules, unlike those described and claimed herein.

The sequence does, however, suggest a structure similar to that possessed by tenascin, as well as a collagen like domain.

The ability of these substantially pure receptor like TGF-β1 binding glycoproteins to bind TGF-β1 renders them useful in a number of ways. As indicated by the foregoing experiments, all three molecules bound to TGF-β1 on a column. As such, each can be used as a "probe" to detect TGF-β1 in a sample. Contact of the sample with the purified glycoprotein, followed by analysis for binding provides an assay method for TGF-β1. In addition, the ability of the glycoproteins to bind TGF-β1 makes them useful as therapeutic agents for preventing the binding of TGF-β1 to a cell with an actual receptor, thereby inhibiting the effect of the TGF-β1 if a sufficient amount of the glycoprotein is added. Other uses for the materials, such as an immunogen for production of antibodies, will be clear to the artisan and need not be set forth here.

Isolation of cDNA, as described herein, puts the artisan in possession of its complementary structure, as the complementary nature of DNA is well known. The deciphering of the amino acid sequence and the cDNA sequence will be seen to put the artisan in possession of the tools to isolate the genomic DNA sequence coding for the TGF-β1 binding protein monomer. To the same end, conventional techniques of microbioloby may be used to transfect cells, be they prokaryotic or eukaryotic, with the coding DNA (genomic or complementary). COS cells may be mentioned as one example of the type of cell which can be so transformed, but other cell types are readily accessible to the skilled artisan, and need not be discussed further.

Any cell receptive to transformation with the subject nucleic acid sequences will be seen to be capable of coding the 35–40 kd monomer. Those cells possessing the means to dimerize and trimerize the monomers will be capable of producing the di and trimers discussed herein.

It is well known that nucleic acid sequences can be used as probes for those cells which express the binding protein. Such antisense sequences may also be used to bind to and inhibit the expression of the binding protein when this is appropriate. Other uses of these sequences will be clear to the skilled artisan.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule, the complementary sequence of which hybridizes to SEQ ID NO: 5 at 0.5×SSC, 0.1% SDS at 50° C.

2. The isolated nucleic acid molecule of claim 1, wherein said isolated nucleic acid molecule is cDNA.

3. The isolated nucleic acid molecule of claim 1, wherein said isolated nucleic acid molecule is gDNA having a sequence coding for TGF-β1 binding protein.

4. The isolated nucleic acid molecule of claim 1, wherein said isolated nucleic acid molecule is mRNA.

5. An isolated nucleic acid molecule which encodes a TGFβ1-binding protein, wherein said protein has a molecular weight of 35–40 kD as determined by SDS-PAGE, and the amino acid sequence of the protein encoded by the isolated nucleic acid molecule having the nucleotide sequence of SEQ ID NO: 5.

6. The isolated nucleic acid molecule of claim 5, having the nucleotide sequence of SEQ ID NO: 5.

7. Isolated cell transfected with the nucleic acid molecule of claim 5.

8. The cell of claim 7, wherein said cell is a COS cell.

* * * * *

UNITED STATES PATENT AND TRADEMARK OFFICE
CERTIFICATE OF CORRECTION

PATENT NO. : 5,731,200

DATED : March 24, 1998

INVENTOR(S) : Ichijo et al.

It is certified that error appears in the above-indentified patent and that said Letters Patent is hereby corrected as shown below:

In column 7, line 32, delete the phrase -- P* is hydroxyproline, and --.

Signed and Sealed this

Ninth Day of November, 1999

Q. TODD DICKINSON

Attest:

Attesting Officer                Acting Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( x i ) SEQUENCE DESCRIPTION: SEQ ID NO: 1:

Tyr Leu Gly Gly Ser His Gly Ser Phe Ala
              5                       10

( 2 ) INFORMATION FOR SEQ ID NO: 2:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( x i ) SEQUENCE DESCRIPTION: SEQ ID NO: 2:

Val Asp Leu Val Asp Phe Glu Gly Asn His Gln Phe Ala
                  5                       10

( 2 ) INFORMATION FOR SEQ ID NO: 3:

( i ) SEQUENCE CHARACTERISTICS:
( A ) LENGTH: 14 amino acids
( B ) TYPE: amino acid ( D ) TOPOLOGY: linear ( i i ) MOLECULE TYPE: protein ( x i ) SEQUENCE DESCRIPTION: SEQ ID NO: 3:

Val Val Gly Leu Glu Gly Ser Asp Lys Leu Ser Ile Leu Arg
            5                           10

( 2 ) INFORMATION FOR SEQ ID NO: 4:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 4:

Val Phe Gly Ser Gln Leu Gly Glu
            5

( 2 ) INFORMATION FOR SEQ ID NO: 5:

( i ) SEQUENCE CHARACTERISTICS:
      ( A ) LENGTH: 1196 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 5:

```
GCG ATG GAC ACA CGC GGA GTG GCC GCG GCC ATG AGG CCC CTG GTC CTG      48
Ala Met Asp Thr Arg Gly Val Ala Ala Ala Met Arg Pro Leu Val Leu
                      5               10                      15

CTC GTT GCC TTC CTG TGC ACC GCA GCC CCA GCC CTC GAC ACC TGT CCA      96
Leu Val Ala Phe Leu Cys Thr Ala Ala Pro Ala Leu Asp Thr Cys Pro
                10              15                  20

GAG GTC AAG GTG GTG GGT CTG GAG GGC TCG GAC AAG CTC TCC ATC CTC     144
Glu Val Lys Val Val Gly Leu Glu Gly Ser Asp Lys Leu Ser Ile Leu
            25                  30                  35

CGA GGC TGC CCG GGG CTG CCT GGA GCC GCA GGG CCC AAG GGA GAG GCG     192
Arg Gly Cys Pro Gly Leu Pro Gly Ala Ala Gly Pro Lys Gly Glu Ala
        40                  45                  50

GGC GCC AGT GGA CCG AAG GGA GGA CAA GGC CCT CCC GGA GCC CCT GGG     240
Gly Ala Ser Gly Pro Lys Gly Gly Gln Gly Pro Pro Gly Ala Pro Gly
    55                  60                  65

GAG CCA GGA CCC CCC GGG CCC AAA GGA GAC CGA GGG GAG AAG GGC GAG     288
Glu Pro Gly Pro Pro Gly Pro Lys Gly Asp Arg Gly Glu Lys Gly Glu
70                  75                  80                  85

CCT GGA CCA AAA GGA GAG TCT TGG GAA ACC GAG CAG TGT CTC ACA GGA     336
Pro Gly Pro Lys Gly Glu Ser Trp Glu Thr Glu Gln Cys Leu Thr Gly
                90                  95                 100

CCT CGG ACC TGC AAG GAG CTG CTG ACC AGG GGG CAC ATT CTG AGC GGC     384
Pro Arg Thr Cys Lys Glu Leu Leu Thr Arg Gly His Ile Leu Ser Gly
            105                 110                 115

TGG CAC ACC ATC TAC CTG CCA GAC TGC AGG CCC CTG ACG GTG CTG TGT     432
Trp His Thr Ile Tyr Leu Pro Asp Cys Gln Pro Leu Thr Val Leu Cys
        120                 125                 130

GAC ATG GAC ACG GAT GGC GGG GGG TGG ACC GTT TTC CAG CGC AGG AGC     480
Asp Met Asp Thr Asp Gly Gly Gly Trp Thr Val Phe Gln Arg Arg Ser
    135                 140                 145

GAC GGG TCG GTG GAC TTC TAC CGG GAC TGG GCC GCG TAC AAG CGG GGC     528
Asp Gly Ser Val Asp Phe Tyr Arg Asp Trp Ala Ala Tyr Lys Arg Gly
150                 155                 160                 165

TTC GGC AGT CAG CTG GGA GAG TTC TGG CTG GGG AAC GAC CAC ATC CAC     576
```

-continued

| | | | | | | | | | | | | | | | | |
|---|---|---|---|---|---|---|---|---|---|---|---|---|---|---|---|---|
| Phe | Gly | Ser | Gln | Leu 170 | Gly | Glu | Phe | Trp 175 | Leu | Gly | Asn | Asp | His | Ile 180 | His | |
| GCC Ala | CTG Leu | ACG Thr | GCC Ala 185 | CAG Gln | GGA Gly | ACC Thr | AAT Asn | GAG Glu 190 | CTC Leu | CGG Arg | GTG Val | GAC Asp | CTC Leu 195 | GTG Val | GAC Asp | 624 |
| TTC Phe | GAG Glu | GGC Gly 200 | AAC Asn | CAC His | CAG Gln | TTT Phe | GCC Ala 205 | AAG Lys | TAC Tyr | AGG Arg | TCC Ser | TTC Phe 210 | CAG Gln | GTG Val | GCA Ala | 672 |
| GAC Asp | GAG Glu 215 | GCA Ala | GAG Glu | AAG Lys | TAC Tyr | ATG Met 220 | CTG Leu | GTC Val | CTG Leu | GGA Gly | GCC Ala 225 | TTT Phe | GTA Val | GAG Glu | GGC Gly | 720 |
| AAT Asn 230 | GCA Ala | GGT Gly | GAT Asp | TCC Ser | CTG Leu 235 | ACG Thr | TCC Ser | CAC His | AAC Asn | AAC Asn 240 | AGC Ser | CTG Leu | TTC Phe | ACC Thr | ACC Thr 245 | 768 |
| AAA Lys | GAC Asp | CAG Gln | GAC Asp | AAC Asn 250 | GAC Asp | CAG Gln | TAC Tyr | GCC Ala | TCA Ser 255 | AAT Asn | TGT Cys | GCA Ala | GTG Val | CTG Leu 260 | TAC Tyr | 816 |
| CAG Gln | GGA Gly | GCC Ala | TGG Trp 265 | TGG Trp | TAC Tyr | AAC Asn | AGC Ser | TGT Cys 270 | CAC His | GTG Val | TCC Ser | AAC Asn | CTG Leu 275 | AAC Asn | GGC Gly | 864 |
| CGC Arg | TAC Tyr | CTC Leu 280 | GGG Gly | GGC Gly | TCG Ser | CAC His | GGG Gly 285 | AGC Ser | TTT Phe | GCA Ala | AAC Asn | GGC Gly 290 | GTC Val | AAC Asn | TGG Trp | 912 |
| AGT Ser | TCG Ser 295 | GGG Gly | AAA Lys | GGG Gly | TAC Tyr | AAC Asn 300 | TAC Tyr | AGC Ser | TAC Tyr | AAG Lys | GTG Val 305 | TCG Ser | GAG Glu | ATG Met | AAG Lys | 960 |
| TTT Phe 310 | CGG Arg | GCC Ala | ACC Thr | | | | | | | | | | | | | 972 |

```
TAGGGCGGGA CAGTGCTTCC AGAACCCTCC CTGGGGAGGG GCCACGGGGC TCCCGCTCAC    1032

TATCCGCCCG GGTGTGAAGG GCCACATCCC AACCCTGGGG GGCGGCCATG CCCTCTGCAC    1092

CTCCACCAGC TTCCAATCTT CTGTCCCTCT CAGGAGGACA AGAGTGACCG TTACTCCAGC    1152

AACATGTATT CTCAATAAAG ACACTTGCTT ACCCAAAAAA AAAA                       1196
```

( 2 ) INFORMATION FOR SEQ ID NO: 6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( i x ) FEATURE:
        ( D ) OTHER INFORMATION: Xaa is hydroxyproline ( x i ) SEQUENCE DESCRIPTION: SEQ ID NO: 6:

Cys  Xaa  Gly  Leu  Xaa  Gly  Ala  Ala  Gly  Pro
                             5

( 2 ) INFORMATION FOR SEQ ID NO: 7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

Asp  Trp  Ala  Ala  Tyr
              5

( 2 ) INFORMATION FOR SEQ ID NO: 8:

( i ) SEQUENCE CHARACTERISTICS:
      ( A ) LENGTH: 41 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 8:

Arg Gly Phe Gly Ser Gln Leu Gly Glu Phe Trp Leu Gly Asn Asp His
                 5                  10                 15
Ile His Ala Leu Thr Ala Gln Gly Thr Asn Glu Leu Xaa Val Asp Leu
             20                  25                 30
Val Phe Glu Gly Asn His Gln Phe Ala
         35              40

( 2 ) INFORMATION FOR SEQ ID NO: 9:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 9:

Gln Leu Gly Glu Phe Trp
                 5

( 2 ) INFORMATION FOR SEQ ID NO: 10:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 10:

Phe Glu Gly Asn His Gln Phe
                 5

( 2 ) INFORMATION FOR SEQ ID NO: 11:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 11:

CARYTNGGNG ARTTYTGG                                                    18

( 2 ) INFORMATION FOR SEQ ID NO: 12:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 12:

RAAYTGRTGR TTNCCYTCRA A                                                21

( 2 ) INFORMATION FOR SEQ ID NO: 13:

(   i   ) SEQUENCE CHARACTERISTICS:
   ( A ) LENGTH: 45 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 13:

TTCTGGCTGG GGAACGACCA CATCCACGCC CTGACGGCCC AGGGT       45

( 2 ) INFORMATION FOR SEQ ID NO: 14:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 14:

GAAGTCCACG AGGTCCACCC GGAGCTCATT GGTTCCCTGG GCCGT       45